(12) United States Patent
Moon et al.

(10) Patent No.: US 10,390,819 B2
(45) Date of Patent: Aug. 27, 2019

(54) AUTOMATIC SUTURING HOOK APPARATUS HAVING INCISION FUNCTION

(71) Applicant: INJE UNIVERSITY INDUSTRY-ACADEMIC COOPERATION FOUNDATION, Gimhae-si, Gyeongsangnam-do (KR)

(72) Inventors: Sung Hyuk Moon, Busan (KR); Won Jae Kim, Daegu (KR); Su Ho Lim, Daegu (KR)

(73) Assignee: INJE UNIVERSITY INDUSTRY-ACADEMIC COOPERATION FOUNDATION, Gimhae-si, Gyeongsangnam-do (KR)

( * ) Notice: Subject to any disclaimer, the term of this patent is extended or adjusted under 35 U.S.C. 154(b) by 301 days.

(21) Appl. No.: 15/518,245

(22) PCT Filed: Oct. 7, 2015

(86) PCT No.: PCT/KR2015/010624
§ 371 (c)(1),
(2) Date: Apr. 11, 2017

(87) PCT Pub. No.: WO2016/060406
PCT Pub. Date: Apr. 21, 2016

(65) Prior Publication Data
US 2017/0319382 A1 Nov. 9, 2017

(30) Foreign Application Priority Data
Oct. 15, 2014 (KR) .......................... 10-2014-0138978

(51) Int. Cl.
*A61B 17/04* (2006.01)
*A61F 9/007* (2006.01)
(Continued)

(52) U.S. Cl.
CPC .......... *A61B 17/0469* (2013.01); *A61B 17/04* (2013.01); *A61B 17/062* (2013.01);
(Continued)

(58) Field of Classification Search
CPC ................ A61B 17/04; A61B 17/0469; A61B 2017/0472; A61B 17/062; A61F 9/007
See application file for complete search history.

(56) References Cited

U.S. PATENT DOCUMENTS

| 5,454,823 A | 10/1995 | Richardson et al. |
| 2007/0233126 A1 | 10/2007 | Hur |

(Continued)

FOREIGN PATENT DOCUMENTS

| JP | 2011-509121 A | 3/2011 |
| JP | 2011-147771 A | 8/2011 |

(Continued)

OTHER PUBLICATIONS

International Search Report for PCT/KR2015/010624 mailed Jan. 27, 2016 from Korean Intellectual Property Office.

*Primary Examiner* — Sarah A Simpson
(74) *Attorney, Agent, or Firm* — Revolution IP, PLLC (57) ABSTRACT

An automatic suturing hook apparatus comprises a main body having a movement hole formed on one side surface thereof and having a first protrusion hole formed on the front end thereof; a needle part which is provided inside the main body and protrudes from the first protrusion hole; a slide body which slidably moves through the movement hole from one side surface of the main body to the front end or rear end of the main body and comes into close contact with the front end of the main body; a slide part which is provided inside the main body and slidably moves the needle part provided inside the main body to the outside of the main body; and a first trigger which is provided at the bottom of the rear end of the main body and operates the slide part which is provided inside the main body.

8 Claims, 5 Drawing Sheets

(51) Int. Cl.
  *A61B 17/062*  (2006.01)
  *A61B 17/3209*  (2006.01)
  *A61B 17/06*  (2006.01)
  *A61B 90/00*  (2016.01)

(52) U.S. Cl.
  CPC .......... *A61F 9/007* (2013.01); *A61B 17/3209* (2013.01); *A61B 2017/0472* (2013.01); *A61B 2017/0608* (2013.01); *A61B 2017/06057* (2013.01); *A61B 2017/06095* (2013.01); *A61B 2090/034* (2016.02)

(56) References Cited

U.S. PATENT DOCUMENTS

2009/0177031 A1* 7/2009 Surti .................. A61B 1/00087
  600/106
2011/0178528 A1  7/2011 Kostrzewski

FOREIGN PATENT DOCUMENTS

| KR | 10-1997-0025565 A | 6/1997 |
| KR | 10-2006-0023718 A | 3/2006 |
| KR | 2015/010624 | 1/2016 |
| WO | 2009/089101 A2 | 7/2009 |

* cited by examiner

AUTOMATIC SUTURING HOOK APPARATUS HAVING INCISION FUNCTION

CROSS REFERENCE TO PRIOR APPLICATIONS

This application is a National Stage Application of PCT International Patent Application No. PCT/KR2015/010624 filed on Oct. 7, 2015, under 35 U.S.C. § 371, which claims priority to Korean Patent Application No. 10-2014-0138978 filed on Oct. 15, 2014, which are all hereby incorporated by reference in their entirety.

TECHNICAL FIELD

The present invention relates to an automatic suturing hook apparatus having an incision function, and more particularly, to an automatic suturing apparatus having an incision function, which is capable of, in strabismus surgery, incising the extraocular muscle adhered to an eyeball and fixing a suture thread to the incised extraocular muscle.

BACKGROUND ART

The basic principle of strabismus surgery is to arrange an eyeball by changing a force of the extraocular muscle adhered to the eyeball. A representative surgical method of changing the force of the extraocular muscle is a method, whereby the extraocular muscle is detached from an original attachment part and then is re-attached to a retrodisplacement position to weaken force or a part of the extraocular muscle is resected and then is re-attached to the original attachment part to reinforce force. Thus, a procedure of detaching the extraocular muscle from the sclera during strabismus surgery is an essential surgical technology.

In lateral rectus recession surgery as an example of strabismus surgery, a muscle hook is inserted between the muscle and the sclera right behind an attachment part, the muscle is lifted to fix a thread to the extraocular muscle adjacent to the attachment part in a horizontal direction and then the muscle is detached from the attachment part and then, the muscle is re-attached to the desired sclera by using a needle of the fixed suture thread, thereby finishing lateral rectus recession surgery.

However, when adhesion of surrounding tissues is severe due to thyroid ophthalmopathy, restrictive strabismus or re-surgery, the muscle is not well relaxed to hang the suture thread to the attachment part by using the muscle hook. Thus, it is difficult to secure a clear view during surgery, and there is a high possibility that the needle perforate the sclera.

In addition, the position of the muscle through which the suture thread passes, affects the amount of strabismus calibration, and currently, the amount of surgery according to a strabismus angle is changed according to the preference of an operator such that integration of a consistent calibration amount is required.

The background art of the present invention is disclosed in Korea Patent Laid-open Publication No. 10-1997-025565 (published on Jun. 24, 1997).

DETAILED DESCRIPTION OF THE INVENTION

Technical Problem

The present invention provides an automatic suturing hook apparatus having an incision function, which is capable of making a consistent strabismus calibration amount, reducing danger of perforating the sclera in strabismus surgery, where it is difficult to secure a clear view during surgery, and by a one-time manipulation, fixing a suture thread and incising the muscle.

Technical Solution

According to an aspect of the present invention, there is provided an automatic suturing hook apparatus having an incision function, including: a man body having a movement hole formed on one side surface thereof and having a first protrusion hole formed on the front end thereof; a needle part which is provided inside the main body and protrudes from the first protrusion hole; a slide body which slidably moves through the movement hole from one side surface of the main body to the front end or rear end of the main body and comes into close contact with the front end of the main body; a slide part which is provided inside the main body and slidably moves the needle part provided inside the main body to the outside of the main body; and a first trigger which is provided at the bottom of the rear end of the main body and operates the slide part which is provided inside the main body.

A second protrusion hole may be formed in the main body to be spaced apart from the first protrusion hole, and the automatic suturing hook apparatus may further include: a cutter which is provided at a lower portion of the needle part inside the main body and protrudes toward the second protrusion hole; and a second trigger which is disposed adjacent to the first trigger and slidably moves the cutter protruding toward the second protrusion hole.

The slide body may have a "ㄱ" shape and may include a movement part which is inserted into the movement hole of the main body and slidably moves, and an adhesion part which is bent from one end of the movement part at a right angle and adhered to the front end of the main body, and a gripping button through which a user grips the movement part to slidably move and which protrudes from a side surface of the movement part.

A movement long hole, through which the gripping button formed on the slide body slidably moving through the movement hole slidably moves, may be formed on one side surface of the main body. The slide part may include: a slide bar which is connected to the first trigger and slidably moves from an inside of the main body forwards or backwards due to an operation of the first trigger; a first pivoting part which is connected to the slide bar and rotated in a movement direction of the slide bar; and a second pivoting part which connects the first pivoting part to the needle part, transfers rotation of the first pivoting part to the needle part and protrudes the needle part toward an outside of the main body through the first protrusion hole.

The slide bar may have a rectangular plate shape, and a plurality of protrusions may be formed on both side surfaces of the slide bar to be spaced apart from one another at equal intervals, and the first pivoting part may include a first gear and a second gear provided below both side surfaces of the slide bar and a connection shaft connecting the first gear to the second gear, and the second pivoting part may cross lower portions of the first gear and the second gear and may include a third gear and a fourth gear connecting the first gear and the second gear to the needle part, and a rotation shaft which passes through central parts of the third gear and the fourth gear and through which the third gear and the fourth gear are mounted inside the main body.

The needle part may include: a first case and a second case having one side surfaces on which a plurality of insertion grooves into which sawteeth of the third gear and sawteeth of the fourth gear are inserted, therein and spaced apart from one another; and a first needle and a second needle provided inside the first case and the second case and having one ends protruding toward an outside of the first case and an outside of the second case and connected to each other by using a suture thread.

The first needle and the second needle may be rounded from one ends to the other ends, and through long holes through which the suture thread passes, may be formed in bottom surfaces of the first case and the second case. The cutter may be connected to the second trigger by using a connection member, and due to rotation of the connection member, the cutter may slidably move and protrude toward the outside of the main body.

Effect of the Invention

An automatic suturing hook apparatus having an incision function according to the present invention has the following effects.

First, surgery can be conducted without danger of perforating the sclera in strabismus surgery, where it is difficult to secure a clear view during surgery, and by a one-time manipulation, a suture thread can be fixed, and the extraocular muscle adhered to an eyeball can be incised so that the surgery time can be shortened.

Second, the suture thread is fixed to the muscle of a consistent position of an attachment part of the extraocular muscle so that it is suitable to make a consistent strabismus calibration amount, and a procedure is simple and easy so that an ophthalmologist who is not a strabismus expert can conduct surgery easily. Also, muscle pulling is small so that muscle tears or muscle missing can be prevented from occurring during strabismus surgery.

BEST MODE

Hereinafter, exemplary embodiments of the present invention will be described in detail with reference to the accompanying drawings. Prior to this, the terms or words used in the present specification and claims should not be interpreted to limiting in a general or dictionary sense but should be interpreted in a sense and concept that complies with the technical spirit of the invention based on the principle that the inventor can define concepts of the terms properly so as to describe his/her own invention in a best manner.

Figure 1:
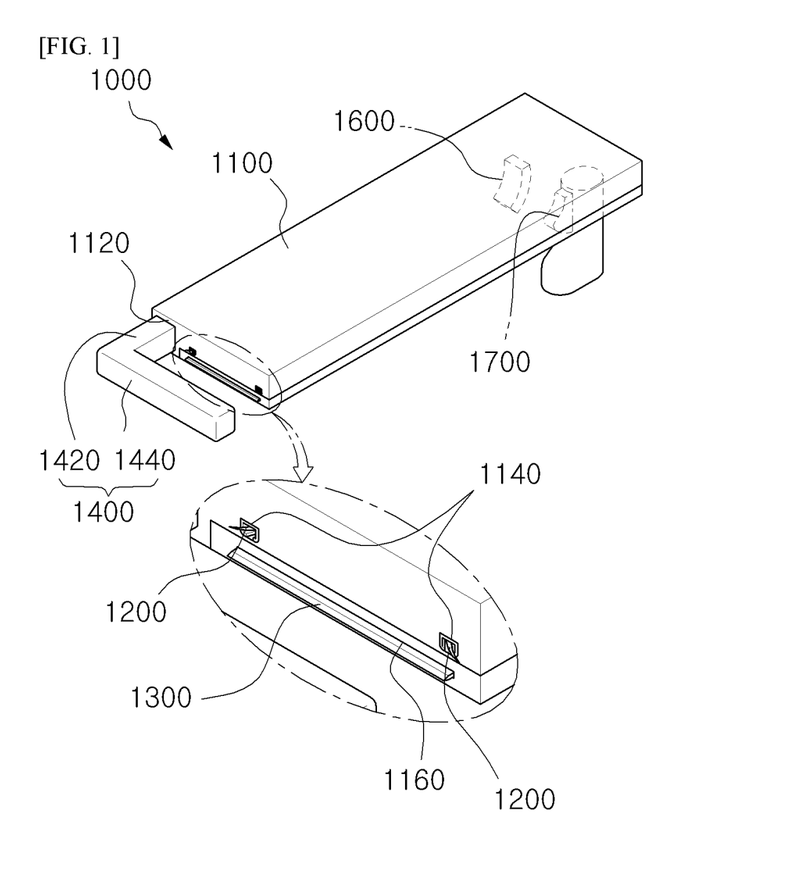
FIG. 1 is a view schematically illustrating an automatic suturing hook apparatus having an incision function according to an embodiment of the present invention.
Figure 2:
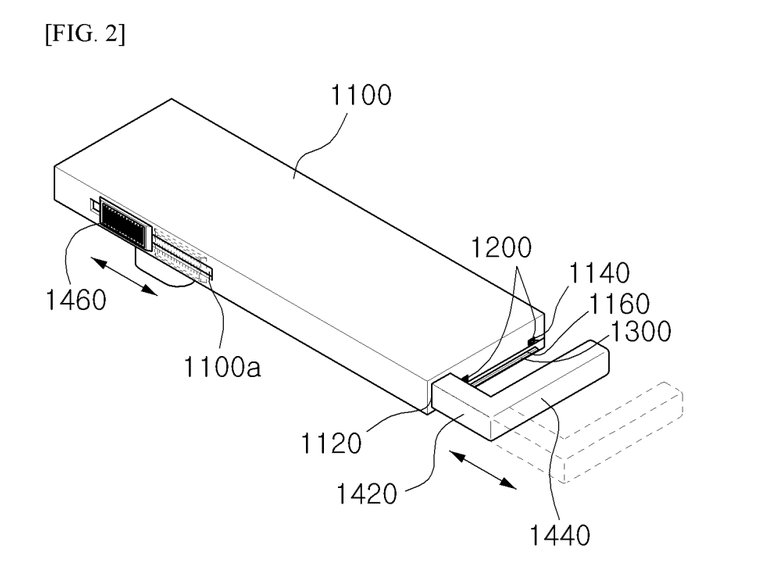
FIG. 2 is a view illustrating the automatic suturing hook apparatus having the incision function illustrated in FIG. 1 from a different angle.
Figure 3:
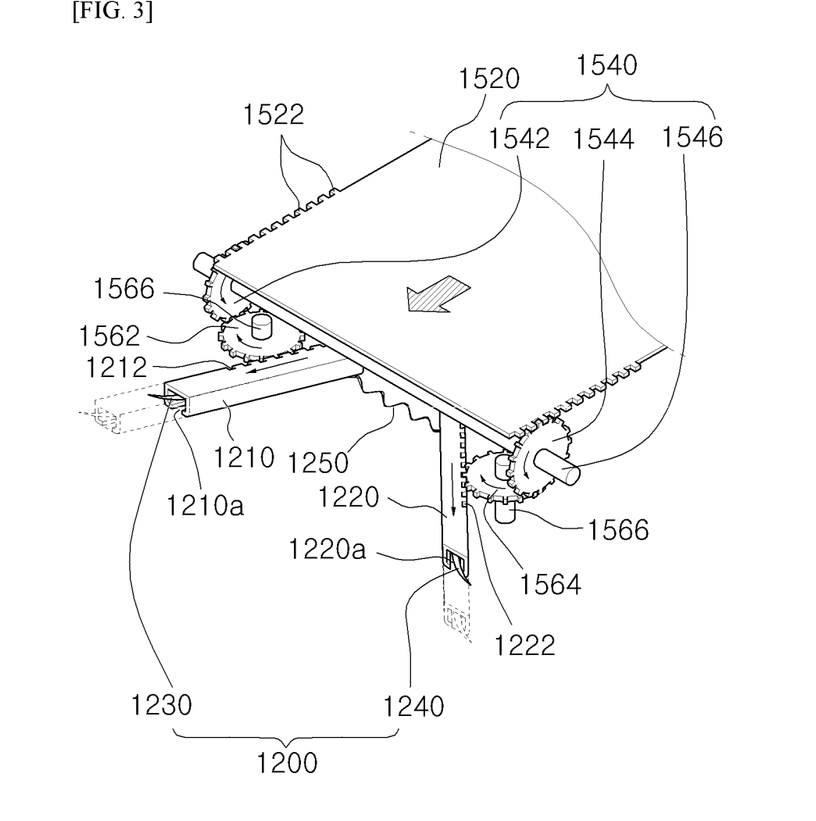
FIG. 3 is a view schematically illustrating a state in which a needle part is connected to a slide part and a first trigger and operates.

FIG. 1 is a view schematically illustrating an automatic suturing hook apparatus having an incision function according to an embodiment of the present invention, and FIG. 2 is a view illustrating the automatic suturing hook apparatus having the incision function illustrated in FIG. 1 from a different angle, and FIG. 3 is a view schematically illustrating a state in which a needle part is connected to a slide part and a first trigger and operates.

Figure 4:
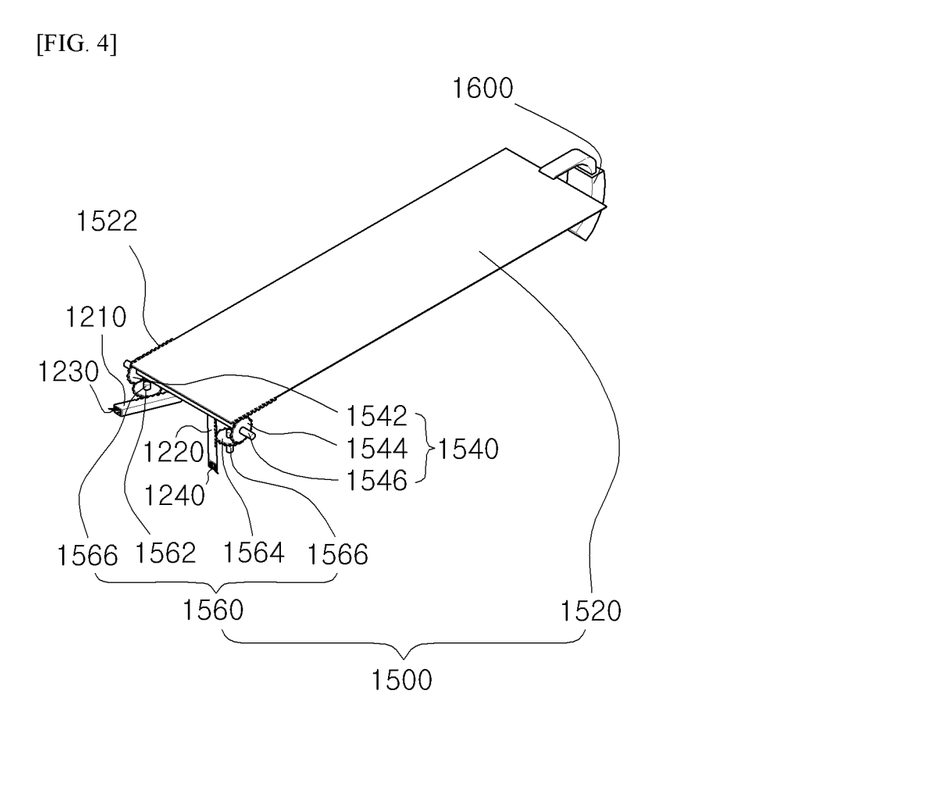
FIG. 4 is a view schematically illustrating a state in which a cutter is connected to a second trigger by using a connection member and operates.
Figure 5:
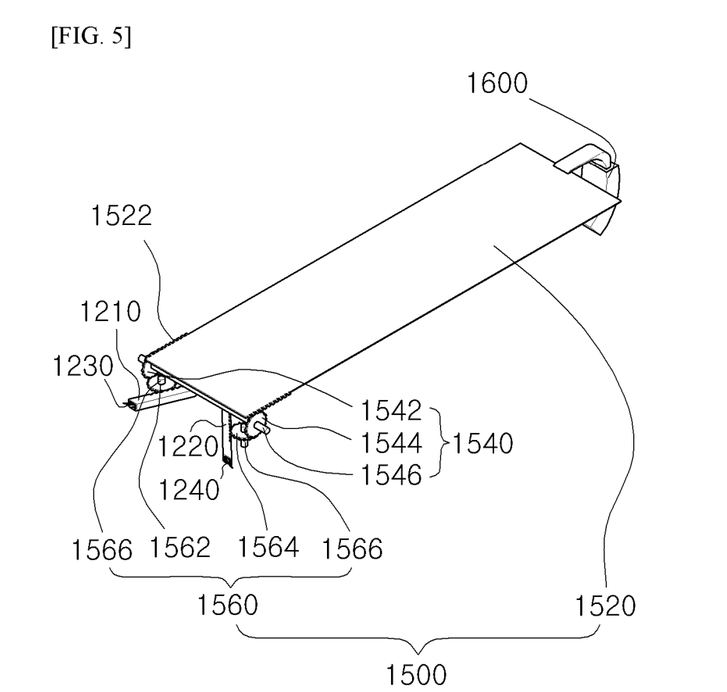
FIG. 5 is an enlarged view of a state in which the needle part illustrated in FIG. 3 slidably moves.
Figure 6:
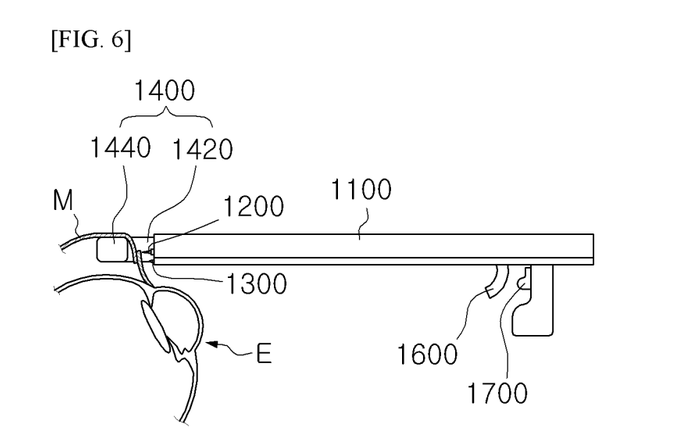
FIG. 6 is a view of a state in which a suture thread is fixed to the extraocular muscle after the extraocular muscle is incised by using the automatic suturing hook apparatus having the incision function of FIG. 1.

FIG. 4 is a view schematically illustrating a state in which a cutter is connected to a second trigger by using a connection member and operates, and FIG. 5 is an enlarged view of a state in which the needle part illustrated in FIG. 3 slidably moves, and FIG. 6 is a view of a state in which a suture thread is fixed to the extraocular muscle after the extraocular muscle is incised by using the automatic suturing hook apparatus having the incision function of FIG. 1.

Referring to the drawings, an automatic suturing hook apparatus 1000 having an incision function according to an embodiment of the present invention includes a main body 1100, a needle part 1200, a cutter 1300, a slide body 1400, a slide part 1500, a first trigger 1600, and a second trigger 1700.

The main body 1100 has a rectangular shape, and a movement hole 1120 is formed at one side surface of a front end of the main body 1100, and a first protrusion hole 1140 and a second protrusion hole 1160 are formed on the front end of the main body 1100 having the movement hole 1120 therein.

The needle part 1200 and the cutter 1300 are provided inside the main body 1100, and the needle part 1200 protrudes from the inside of the main body 1100 outwards through the first protrusion hole 1140 formed in the main body 1100, and the cutter 1300 protrudes from the inside of the main body 1100 outwards through the second protrusion hole 1160, and the cutter 1300 cuts the extraocular muscle M that comes into close contact with the front end of the main body 1100 while protruding toward the outside of the main body 1100.

The slide body 1400 is inserted into the movement hole 1120, and the slide body 1400 slidably moves through the movement hole 1120 from one side surface of the main body 1100 to the front end or rear end of the main body 1100.

The slide body 1400 has a "⌐" shape, includes a movement part 1420 and an adhesion part 1440, and may further include a gripping button 1460. The movement part 1420 is inserted into the movement hole 1120 of the main body 1100 and slidably moves inside the main body 1100, and the adhesion part 1440 is bent from one end of the movement part 140 at a right angle, and when the movement part 1420 slidably moves to the inside of the main body 1100, the movement part 1420 comes into close contact with the front end of the main body 1100. The gripping button 1460 protrudes toward a side surface of the movement part 1420, and the gripping button 1460 is a part gripped by a user to slidably move the movement part 1420, and because the user moves the gripping button 1460 by his/her own finger, the movement part 1420 slidably moves from the inside of the main body 1100 outwards or slidably moves from the outside of the main body 1100 inwards.

A movement long hole 1100a, through which the gripping button 1460 formed on the slide body 1400 slidably moving through the movement hole 1120 slidably moves, may be formed on one side surface of the main body 1100.

The slide body 1400 slidably moves from one side surface of the main body 1100 and adheres the extraocular muscle M adhered to an eyeball E by using the adhesion part 1440 to the front end of the main body 1100 to fix the extraocular muscle M to the front end of the main body 1100. The slide body 1400 adheres the extraocular muscle M to the front end of the main body 1100 and fixes the extraocular muscle M thereto so that the extraocular muscle M can be conveniently cut by using the cutter 1300 that will be described below.

The needle part 1200 provided inside the main body 1100 protrudes from the inside of the main body 1100 outwards through the slide part 1500, and the slide part 1500 slidably moves the needle part 1200 to the outside of the main body 1100.

The slide part 1500 includes a slide bar 1520, a first pivoting part 1540, and a second pivoting part 1560. The slide bar 1520 has a rectangular plate shape, and a plurality of protrusions 1522 are formed on both side surfaces of the slide bar 1520 to be spaced apart from one another at equal intervals. The slide bar 1520 is connected to the first trigger 1600 that will be described below, and due to an operation of the first trigger 1600, the slide bar 1520 slidably moves from the inside of the main body 1100 to the front end or rear end of the main body 1100.

The first pivoting part 1540 is connected to the slide bar 1520, and when the slide bar 1520 slidably moves, the first pivoting part 1540 is rotated in a movement direction of the slide bar 1520. The first pivoting part 1540 includes a first gear 1542, a second gear 1544, and a connection shaft 1546. The first gear 1542 and the second gear 1544 are provided below both side surfaces of the slide bar 1520, and the first gear 1542 and the second gear 1544 are rotated in the movement direction of the slide bar 1520 by using protrusions 1522 of the slide bar 1520. The first gear 1542 and the second gear 1544 that are spaced apart from each other, are connected to each other by using the connection shaft 1546 and are mounted inside the main body 1100.

The first pivoting part 1540 is connected to the second pivoting part 1560, and the second pivoting part 1560 connects the first pivoting part 1540 to the needle part 1200 and transfers rotation of the first pivoting part 1540 to the needle part 1200.

The second pivoting part 1560 includes a third gear 1562, a fourth gear 1564, and a rotation shaft 1566. The third gear 1562 crosses the first gear 1542, and the fourth gear 1564 crosses the second gear 1544 so that the third gear 1562 and the fourth gear 1564 are rotated by rotation of the first gear 1542 and the second gear 1544. The rotation shaft 1566 through which the third gear 1562 and the fourth gear 1564 are mounted inside the main body 1100, passes through central parts of the third gear 1562 and the fourth gear 1564, and the third gear 1562 and the fourth gear 1564 are rotated around the rotation shaft 1566 by using the first gear 1542 and the second gear 1544.

The second pivoting part 1560 transfers rotation of the first pivoting part 1540 to the needle part 1200, and the needle part 1200 connected to the second pivoting part 1560 includes a first case 1210, a second case 1220, a first needle 1230, and a second needle 1240.

The first case 1210 and the second case 1220 come into close contact with the third gear 1562 and the fourth gear 1564, respectively, and a plurality of insertion grooves 1212 and 1222 into which sawteeth of the third gear 1562 and sawteeth of the fourth gear 1564 are inserted, are provided in one side surfaces of the first case 1210 and the second case 1220 and are spaced apart from one another, and due to the sawteeth of the rotating third gear 1562 and fourth gear 1564, the first case 1210 and the second case 1220 slidably move in a rotation direction of the third gear 1562 and the fourth gear 1564.

A first needle 1230 and a second needle 1240 are provided inside the first case 1210 and the second case 1220 that slidably move due to the third gear 1562 and the fourth gear 1564. The first needle 1230 and the second needle 1240 are connected to each other by using a suture thread, and one ends of the first needle 1230 and the second needle 1240 protrude toward the outside of the first case 1210 and the outside of the second case 1220, respectively.

One ends of the first needle 1230 and the second needle 1240 protrude toward the outside of the first case 1210 and the outside of the second case 1220, respectively, so that, when the first case 1210 and the second case 1220 move slidably and are exposed to the outside of the main body 1100, the first needle 1230 and the second needle 1240 are inserted into the extraocular muscle and are fixed thereto.

The first needle 1230 and the second needle 1240 may be rounded from one ends thereof to the other ends thereof. As the first needle 1230 and the second needle 1240 are rounded, the first needle 1230 and the second needle 1240 are fixed to the extraocular muscle M to be inclined from the inside of the extraocular muscle M to the outside thereof. Through long holes 1210*a* and 1220*a* may be formed in bottom surfaces of the first case 1210 and the second case 1220 into which the first needle 1230 and the second needle 1240 are inserted, so that a suture thread 1250 connecting the first needle 1230 to the second needle 1240 passes through the through long holes 1210*a* and 1220*a*.

The needle part 1200 protrudes from the inside of the main body 1100 outwards by using the first trigger 1600 connected to the slide part 1500. The first trigger 1600 may be provided below the rear end of the main body 1100 so that the user can easily grip the first trigger 1600. As the user operates the first trigger 1600, the slide part 1500 provided inside the main body 1100 operates, and the needle part 1200 protrudes toward the outside of the main body 1100.

The second trigger 1700 is disposed adjacent to the first trigger 1600. The second trigger 1700 slidably moves the cutter 1300 that protrudes toward the second protrusion hole 1160, and the second trigger 1700 and the cutter 1300 are connected to each other by using a connection member C, and when the user operates the second trigger 1700, the connection member C is rotated, and the cutter 1300 protrudes toward the outside of the main body 1100, the extraocular muscle M adhered to the front end of the main body 1100 by using the slide body 1400 is cut.

Thus, in strabismus surgery, where it is difficult to secure a clear view during surgery, surgery can be conducted without danger of perforating the sclera, and it is possible to, by a one-time manipulation, fix the suture thread 1250 and incise the extraocular muscle M adhered to the eyeball E, thereby shortening the surgery time. In addition, the suture thread 1250 is fixed to the muscle of a consistent position of an attachment part of the extraocular muscle so that it is suitable to make a consistent strabismus calibration amount, and a procedure is simple and easy so that an ophthalmologist who is not a strabismus expert can conduct surgery easily. Also, muscle pulling is small so that muscle tears or muscle missing can be prevented from occurring during strabismus surgery.

While the present invention has been particularly shown and described with reference to exemplary embodiments thereof, it will be understood by those of ordinary skill in the art that various changes in form and details may be made therein without departing from the spirit and scope of the present invention as defined by the following claims.

INDUSTRIAL APPLICABILITY

The present invention can be used in an automatic suturing apparatus.

The invention claimed is:

1. An automatic suturing hook apparatus having an incision function, comprising:
   a main body having a movement hole formed on one side surface thereof and having a first protrusion hole formed on a front end thereof;
   a needle part which is provided inside the main body and protrudes from the first protrusion hole;
   a slide body which slidably moves through the movement hole from one side surface of the main body to the front end or rear end of the main body and comes into close contact with the front end of the main body;
   a slide part which is provided inside the main body and slidably moves the needle part provided inside the main body to the outside of the main body; and
   a first trigger which is provided at the bottom of the rear end of the main body and operates the slide part which is provided inside the main body,
   wherein a second protrusion hole is formed in the main body to be spaced apart from the first protrusion hole, and
   the automatic suturing hook apparatus further comprises:
   a cutter which is provided at a lower portion of the needle part inside the main body and protrudes toward the second protrusion hole; and
   a second trigger which is disposed adjacent to the first trigger and slidably moves the cutter protruding toward the second protrusion hole.

2. The automatic suturing hook apparatus of claim 1, wherein the cutter is connected to the second trigger by using a connection member, and due to rotation of the connection member, the cutter slidably moves and protrudes toward the outside of the main body.

3. An automatic suturing hook apparatus having an incision function, comprising:
   a main body having a movement hole formed on one side surface thereof and having a first protrusion hole formed on a front end thereof;
   a needle part which is provided inside the main body and protrudes from the first protrusion hole;
   a slide body which slidably moves through the movement hole from one side surface of the main body to the front end or rear end of the main body and comes into close contact with the front end of the main body;
   a slide part which is provided inside the main body and slidably moves the needle part provided inside the main body to the outside of the main body; and
   a first trigger which is provided at the bottom of the rear end of the main body and operates the slide part which is provided inside the main body, wherein the slide body comprises:
   a movement part which is inserted into the movement hole of the main body and slidably moves, and an adhesion part which is bent from one end of the movement part at a right angle, and a gripping button through which a user grips the movement part to slidably move and which protrudes from a side surface of the movement part.

4. The automatic suturing hook apparatus of claim 3, wherein a movement long hole, through which the gripping button formed on the slide body slidably moving through the movement hole slidably moves, is formed on one side surface of the main body.

5. An automatic suturing hook apparatus having an incision function, comprising:
   a main body having a movement hole formed on one side surface thereof and having a first protrusion hole formed on a front end thereof;
   a needle part which is provided inside the main body and protrudes from the first protrusion hole;
   a slide body which slidably moves through the movement hole from one side surface of the main body to the front end or rear end of the main body and comes into close contact with the front end of the main body;
   a slide part which is provided inside the main body and slidably moves the needle part provided inside the main body to the outside of the main body; and
   a first trigger which is provided at the bottom of the rear end of the main body and operates the slide part which is provided inside the main body, wherein the slide part comprises:
   a slide bar which is connected to the first trigger and slidably moves from an inside of the main body forwards or backwards due to an operation of the first trigger;
   a first pivoting part which is connected to the slide bar and rotated in a movement direction of the slide bar; and
   a second pivoting part which connects the first pivoting part to the needle part, transfers rotation of the first pivoting part to the needle part and protrudes the needle part toward an outside of the main body through the first protrusion hole.

6. The automatic suturing hook apparatus of claim 5, wherein the slide bar has a rectangular plate shape, and a plurality of protrusions are formed on both side surfaces of the slide bar to be spaced apart from one another at equal intervals, and the first pivoting part comprises a first gear and a second gear provided below the both side surfaces of the slide bar and a connection shaft connecting the first gear to the second gear, and the second pivoting part crosses lower portions of the first gear and the second gear and comprises a third gear and a fourth gear connecting the first gear and the second gear to the needle part, and a rotation shaft which passes through central parts of the third gear and the fourth gear and through which the third gear and the fourth gear are mounted inside the main body.

7. The automatic suturing hook apparatus of claim 6, wherein the needle part comprises:
   a first case and a second case having one side surface on which a plurality of insertion grooves into which sawteeth of the third gear and sawteeth of the fourth gear are inserted, therein and spaced apart from one another; and
   a first needle and a second needle provided inside the first case and the second case and having one ends protruding toward an outside of the first case and an outside of the second case and connected to each other by using a suture thread.

8. The automatic suturing hook apparatus of claim 7, wherein the first needle and the second needle are formed to be rounded, and through long holes through which the suture thread passes, are formed in bottom surfaces of the first case and the second case.

* * * * *